United States Patent
Sela et al.

(10) Patent No.: US 9,040,047 B2
(45) Date of Patent: May 26, 2015

(54) COMBINATIONS OF ANTI ERBB ANTIBODIES FOR THE TREATMENT OF CANCER

(75) Inventors: Michael Sela, Rehovot (IL); Yosef Yarden, Rehovot (IL); Bilha Schechter, Rehovot (IL); Ruth Maron, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/118,243

(22) PCT Filed: May 16, 2012

(86) PCT No.: PCT/IL2012/050176
§ 371 (c)(1),
(2), (4) Date: Nov. 18, 2013

(87) PCT Pub. No.: WO2012/156975
PCT Pub. Date: Nov. 22, 2012

(65) Prior Publication Data
US 2014/0086917 A1    Mar. 27, 2014

Related U.S. Application Data

(60) Provisional application No. 61/486,362, filed on May 16, 2011.

(51) Int. Cl.
| | |
|---|---|
| C07K 16/00 | (2006.01) |
| A61K 39/395 | (2006.01) |
| C07K 16/28 | (2006.01) |
| C07K 16/32 | (2006.01) |
| A61N 5/10 | (2006.01) |
| A61K 39/00 | (2006.01) |

(52) U.S. Cl.
CPC ..... *A61K 39/39558* (2013.01); *A61K 2039/505* (2013.01); *A61K 2039/507* (2013.01); *C07K 16/2863* (2013.01); *C07K 16/32* (2013.01); *A61N 5/10* (2013.01)

(58) Field of Classification Search
None
See application file for complete search history.

(56) References Cited

U.S. PATENT DOCUMENTS

| | | |
|---|---|---|
| 5,587,458 A | 12/1996 | King et al. |
| 5,693,762 A | 12/1997 | Queen et al. |
| 7,498,142 B2 | 3/2009 | Yarden et al. |
| 2003/0086924 A1 | 5/2003 | Sliwkowski |
| 2003/0170235 A1 | 9/2003 | Cohen |
| 2007/0178102 A1 | 8/2007 | Yarden et al. |
| 2009/0155288 A1 | 6/2009 | Yarden et al. |

FOREIGN PATENT DOCUMENTS

| | | |
|---|---|---|
| WO | WO 2004/032960 | 4/2004 |
| WO | WO 2007/076923 | 7/2007 |
| WO | WO 2008/031531 | 3/2008 |
| WO | WO 2010/022736 | 3/2010 |
| WO | WO 2010/029534 | 3/2010 |
| WO | WO 2011/107957 | 9/2011 |
| WO | WO 2012/059857 | 5/2012 |
| WO | WO 2012/156975 | 11/2012 |

OTHER PUBLICATIONS

Strome et al., The Oncologist, 2007; 12:1084-95.*
Brand et al., Anticancer Res. 2006; 26:463-70.*
International Preliminary Report on Patentability Dated Nov. 28, 2013 From the International Bureau of WIPO Re. Application No. PCT/IL2012/050176.
International Preliminary Report on Patentability Dated Mar. 24, 2011 From the International Bureau of WIPO Re.: Application No. PCT/IL2009/000816.
International Search Report and the Written Opinion Dated Feb. 15, 2010 From the International Searching Authority Re.: Application No. PCT/IL2009/000816.
International Search Report and the Written Opinion Dated Jul. 23, 2012 From the International Searching Authority Re. Application No. PCT/IL2012/050176.
Office Action Dated May 5, 2013 From the Israel Patent Office Re. Application No. 211752 and Its Translation Into English.
Official Action Dated Nov. 1, 2007 From the US Patent and Trademark Office Re.: U.S. Appl. No. 11/342,615.
Official Action Dated Apr. 5, 2013 From the US Patent and Trademark Office Re. U.S. Appl. No. 13/072,839.
Official Action Dated Sep. 6, 2013 From the US Patent and Trademark Office Re. U.S. Appl. No. 13/063,940.

(Continued)

*Primary Examiner* — Sheela J Huff

(57) ABSTRACT

An article-of-manufacture is provided. The article-of-manufacture comprises a packaging material identified for treating cancer, packaging:

(i) an anti-EGFR antibody comprising the CDR sequences of anti EGFR 565 (CNCM Deposit Number I-4262); and
(ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112), or (iii) an anti-EGFR antibody comprising the CDR sequences of anti EGFR 111 (CNCM Deposit Number I-4261); and
(iv) an anti-ErbB-2 antibody comprising the CDR sequences of anti ErbB-2 L431 (CNCM Deposit Number I-4115).

Also provided are pharmaceutical compositions and methods of using the above antibodies as well as other antibody combinations for the treatment of cancer.

19 Claims, 12 Drawing Sheets

(56) References Cited

OTHER PUBLICATIONS

Official Action Dated Sep. 7, 2012 From the US Patent and Trademark Office Re. U.S. Appl. No. 13/072,839.
Official Action Dated Nov. 9, 2010 From the US Patent and Trademark Office Re. U.S. Appl. No. 12/320,207.
Official Action Dated Apr. 10, 2012 From the US Patent and Trademark Office Re. U.S. Appl. No. 13/072,839.
Official Action Dated Apr. 11, 2007 From the US Patent and Trademark Office Re.: U.S. Appl. No. 11/342,615.
Official Action Dated Sep. 17, 2009 From the US Patent and Trademark Office Re.: U.S. Appl. No. 12/320,207.
Official Action Dated Jan. 20, 2010 From the US Patent and Trademark Office Re.: U.S. Appl. No. 12/320,207.
Official Action Dated Jul. 21, 2010 From the US Patent and Trademark Office Re.: U.S. Appl. No. 12/320,207.
Official Action Dated May 22, 2008 From the US Patent Office Re.: U.S. Appl. No. 11/342,615.
Summons to Attend Oral Proceedings Pursuant to Rule 115(1) EPC Dated Jul. 3, 2012 From the European Patent Office Re. Application No. 09787543.9.
Arteaga "The Epidermal Growth Factor Receptor: From Mutant Oncogene in Nonhuman Cancers to Therapeutic Target in Human Neoplasia", Journal of Clinical Oncology, 19(18/Suppl.): 32s-40s, Sep. 15, 2001.
Baselga et al. "Objective Response Rate in A Phase II Multicenter Trial of Pertuzumab (P), A HER2 Dimerization Inhibiting Monoclonal Antibody, in Combination With Trastuzumab (T) in Patients (PTS) With HER2-Positive Metastatic Breast Cancer (MBC) Which Has Progressed During Treatment With T", Journal of Clinical Oncology, Clinical Science Symposium, Oral Presentation, p. 33s: # 1004, 2007.
Beckman et al. "Antibody Constructs in Cancer Therapy. Protein Engineering Strategies to Improve Exposure in Solid Tumors", Cancer, 109: 170-179, 2007.
Ben-Kasus et al. "Cancer Therapeutic Antibodies Come of Age: Targeting Minimal Residual Disease", Molecular Oncology, 1: 42-54, 2007.
Ben-Kasus et al. "Persistent Elimination of ErbB-2/HER2-Overexpressing Tumors Using Combinations of Monoclonal Antibodies: Relevance of Receptor Endocytosis", Proc. Natl. Acad. Sci. USA, XP002562767, 106(9): 3294-3299, Mar. 2009.
Cespedes et al. "Mouse Models in Oncogenesis and Cancer Therapy", Clinical & Translational Oncology, 8(5): 318-329, May 2006.
Chen et al. "An Immunological Approach Reveals Biological Differences Between the Two NDF/Heregulin Receptors, ErbB-3 and ErbB-4", The Journal of Biological Chemistry, 271(13): 7620-7629, 1996.
Dennis "Off by A Whisker", Nature, 442: 739-741, 2006.
Drebin et al. "Monoclonal Antibodies Reactive With Distinct Domains of the Neu Oncogene-Encoded P185 Molecule Exert Synergistic Anti-Tumor Effects In Vivo", Oncogene, 2(3): 273-277, 1988.
Drebin et al. "Monoclonal Antibodies Reactive With Distinct Domains of the Neu Oncogene-Encoded P185 Molecule Exert Synergistic Anti-Tumor Effects In Vivo", Oncogene, 2: 273-277, 1988.
Dugan et al. "HER-2/Neu Expression in Pancreatic Adenocarcinoma: Relation to Tumor Differentiation and Survival", Pancreas, 14(3): 229-236, 1997.
Friedman et al. "Synergistic Down-Regulation of Receptor Tyrosine Kinases by Combinations of mAbs: Implications for Cancer Immunotherapy", Proc. Natl. Acad. Sci. USA, PNAS, 102(6): 1915-1920, 2005.
Fujimori et al. "A Modeling Analysis of Monoclonal Antibody Percolation Through Tumors: A Binding-Site Barrier", Journal of Nuclear Medicine, 31: 1191-1198, 1990.
Goldstein et al. "Biological Efficacy of A Chimeric Antibody to the Epidermal Growth Factor Receptor in A Human Tumor Xenograft Model", Clinical Cancer Research, 1(11): 1311-1318, Nov. 1995.
Harwerth et al. "Monoclonal Antibodies Directed to the ErbB-2 Receptor Inhibit In Vivo Tumour Cell Growth", British Journal of Cancer, 68(6): 1140-1145, Dec. 1993.
Heitner et al. "Selection of Cell Binding and Internalizing Epidermal Growth Factor Receptor Antibodies From A Phage Display Library", Journal of Immunological Methods, 248: 17-30, 2001.
Hurwitz et al. "Suppression and Promotion of Tumor Growth by Monoclonal Antibodies to ErbB-2 Differentially Correlate With Cellular Uptake", Proc. Natl. Acad. Sci. USA, 92(8): 3353-3357, 1995.
Johns et al. "Identification of the Epitope for the Epidermal Growth Factor Receptor-Specific Monoclonal Antibody 806 Reveals That It Preferentially Recognizes An Untethered Form of the Receptor", The Journal of Biological Chemistry, 279(29): 30375-30384, Jul. 16, 2004.
Johnstone et al. "Manipulation and Storage of Immunoglobulins", Immunochemistry in Practice, Blackwell Scientific Publications, 2nd Ed.: 49-50, 1987.
Kamat et al. "Enhanced EGFR Inhibition and Distinct Epitope Recognition by EGFR Antagonistic mAbs C225 and 425", Cancer Biology & Therapy, 7(5): 726-733, May 2008.
Kasprzyk "A Therapy of An Animal Model of Human Gastric Cancer Using A Combination of Anti-ErbB-2 Monoclonal Antibodies", Cancer Research, 52: 2771-2776, 1992.
Kasprzyk et al. "A Therapy of An Animal Model of Human Gastric Cancer Using A Combination of Anti-ErbB-2 Monoclonal Antibodies", Cancer Research, 52(10): 2771-2776, 1992.
Kipriyanov et al. "Recent Advances in the Generation of Bispecific Antibodies for Tumor Immunotherapy", Current Opinion in Drug Discovery & Development, 7(2): 233-242, 2004.
Klapper et al. "A Subclass of Tumor-Inhibitory Monoclonal Antibodies to Erb-2/HER2 Blocks Crosstalk With Growth Factor Receptors", Oncogene, XP001068241, 14(17): 2099-2109, 1997. Table 1.
Klapper et al. "A Subclass of Tumor-Inhibitory Monoclonal Antibodies to ErbB-2/HER2 Blocks Crosstalk With Growth Factor Receptors", Oncogene, 14: 2099-2109, 1997.
Klapper et al. "Tumor-Inhibitory Antibodies to HER-2/ErbB-2 May Act by Recruiting c-CbI and Enhancing Ubiquitination of HER-2[1]", Cancer Research, 60: 3384-3388, 2000.
Larbouret et al. "Combined Cetuximab and Trastuzumab Are Superior to Gemcitabine in the Treatment of Human Pancreatic Carcinoma Xenografts", Annals of Oncology, 21: 98-103, 2010.
Larbouret et al. "Combined Cetuximab and Trastuzumab Are Superior to Gemcitabine in the Treatment of Human Pancreatic Carcinoma Xenografts", Annals of Oncology, XP002679701, 21(1): 93-103, Jan. 2010. Figs.1, 4.
Larbouret et al. "In Vivo Therapeutic Synergism of Anti-Epidermal Growth Factor Receptor and Anti-HER2 Monoclonal Antibodies Against Pancreatic Carcinomas", Clinical Cancer Research, 13: 3356-3362, Jun. 1, 2007.
Larbouret et al. "In Vivo Therapeutic Synergism of Anti-Epidermal Growth Factor Receptor and Anti-HER2 Monoclonal Antibodies Against Pancreatic Carcinomas", Clinical Cancer Research, XP009148159, 13(11): 3356-3362, Jun. 1, 2007.
Lee et al. "Monoclonal Antibody Radiopharmaceuticals: Cationization, Pegylation, Radiometal Chelation, Pharmacokinetics, and Tumor Imaging", Bioconjugate Chemistry, 14: 546-553, 2003.
Leonard et al. "Combination Antibody Therapy With Epratuzumab and Rituximab in Relapsed or Refractory Non-Hodgkin's Lymphoma", Journal of Clinical Oncology, 23(22): 5044-5051, Aug. 1, 2005.
Merimsky et al. "Induction Chemotherapy for Bone Sarcoma in Adults: Correlation of Results With ErbB-4 Expression", Oncology Reports, 10: 1593-1599, 2003.
Nahta et al. "The HER-2-Targeting Antibodies Trastuzumab and Pertuzumab Synergistically Inhibit the Survival of Breast Cancer Cells", Cancer Research, 64: 2343-2346, 2004.
Nielsen et al. "Internalizing Antibodies and Targeted Cancer Therapy: Direct Selection From Phage Display Libraries", Pharmaceutical Science & Technology Today, 3(8): 282-291, Aug. 2000.
Panousis et al. "Engineering and Characterisation of Chimeric Monoclonal Antibody 806 (CH806) for Targeted Immunotherapy of Tumours Expressing DE2-7 EGFR or Amplified EGFR", British Journal of Cancer, 92: 1069-1077, 2005.

(56) References Cited

OTHER PUBLICATIONS

Perera et al. "Treatment of Human Tumor Xenografts With Monoclonal Antibody 806 in Combination With A Prototypical Epidermal Growth Factor Receptor-Specific Antibody Generates Enhanced Antitumor Activity", Clinical Cancer Research, 11(17: 6390-6399, Sep. 1, 2005.

Perera et al. "Treatment of Human Tumor Xenografts With Monoclonal Antibody 806 in Combination With A Prototypical Epidermal Growth Factor Receptor-Specific Antibody Generates Enhanced Antitumor Activity", Clinical Cancer Research, 11: 6390-6399, Sep. 2005.

Persson et al. "[177Lu]Pertuzumab: Experimental Studies on targeting of HER-2 Positive Tumour Cells", European Journal of Nuclear Medicine and Molecular Imaging, 32(12): 1457-1462, 2005.

Rudnick et al. "Affinity and Avidity in Antibody-Based Tumor Targeting", Cancer Biotherapy and Radiopharmaceuticals, 24(2): 155-162, 2009.

Scheuer et al. "Strongly Enhanced Antitumor Activity of Trastuzumab and Pertuzumab Combination Treatment on HER2-Positive Human Xenograft Tumor Models", Cancer Research, 69: 9330-9336, 2009.

Shen et al. "In Vivo Activity of Novel Anti-ErbB2 Antibody ChA21 Alone and With Paclitaxel or Trastuzumab in Breast and Ovarian Cancer Xenograft Models", Cancer Immunology & Immunotherapy, 60: 339-348, 2011.

Slamon et al. "Studies of the HER-2/Neu Proto-Oncogene in Human Breast and Ovarian Cancer", Science, 244(4905): 707-712, 1989.

Slamon et al. "Studies of the HER-2/Neu Proto-Oncogene in Human Breast and Ovarian Cancer", Science, 244: 707-712, May 12, 1989.

Spangler et al. "Combination Antibody Treatment Down-Regulates Epidermal Growth Factor Receptor by Inhibiting Endosomal Recycling", Proc. Natl. Acad. Sci. USA, PNAS, 107(30): 13252-13257, Jul. 27, 2010.

Spiridon et al. "A Comparison of the In Vitro and In Vivo Activities of IgG and F(ab')2 Fragments of A Mixture of Three Monoclonal Anti-Her-2 Antibodies", Clinical Cancer Research, 10: 3542-3551, 2004.

Spiridon et al. "Targeting Multiple Her-2 Epitopes With Monoclonal Antibodies Results in Improved Antigrowth \Activity of A Human Breast Cancer Cell Line In Vitro and In Vivo", Clinical Cancer Research, 8: 1720-1730, 2002.

Spiridon et al. "Targeting Multiple Her-2 Epitopes With Monoclonal Antibodies Results in Improved Antigrowth Activity of A Human Breast Cancer Cell Line In Vitro and In Vivo", Clinical Cancer Research, 8: 1720-1730, 2002.

Stratagene "Gene Characterization Kits", Catalog, Stratagene, p. 39, 1988.

Talmadge et al. "Murine Models to Evaluate Nocel and Conventional Therapeutic Strategies for Cancer", The American Journal of Pathology, 170(3): 793-804, Mar. 2007.

Thurber et al. "Antibody Tumor Penetration: Transport Opposed by Systenic and Antigen-Mediated Clearance", Advanced Drug Delivery Reviews, 60: 1421-1434, 2008.

Tokunaga et al. "Trastuzumab and Breast Cancer: Developments and Current Status", Int. J. Clin. Oncol., 11(3): 199-208, 2006, Abstract.

Troise et al. "Differential Binding of Human Immunoagents and Herceptin to the ErbB2 Receptor", The FEBS Journal, 275: 4967-4979, 2008.

Voskoglou-Nomikos et al. "Clinical Predictive Value of the In Vitro Cell Line, Human Xenograft, and Mouse Allograft Preclinical Cancer Models", Clinical Cancer Research, 9: 4227-4239, Sep. 15, 2003.

Yarden "Biology of HER2 and Its Importance in Breast Cancer", Oncology, 61(suppl 2): 1-13, 2001.

Ye et al. "Augmentation of A Humanized Anti-HER2 mAb 4D5 INduced Growth Inhibition by A Human-Mouse Chimeric Anti-EGF Receptor mAb C225", Oncogene, 18: 731-738, 1999.

*Ex Parte Quayle* Official Action Dated Mar. 25, 2014 From the US Patent and Trademark Office Re. U.S. Appl. No. 13/063,940.

Communication Pursuant to Article 94(3) EPC Dated Oct. 16, 2014 From the European Patent Office Re. Application No. 12726895.1.

* cited by examiner

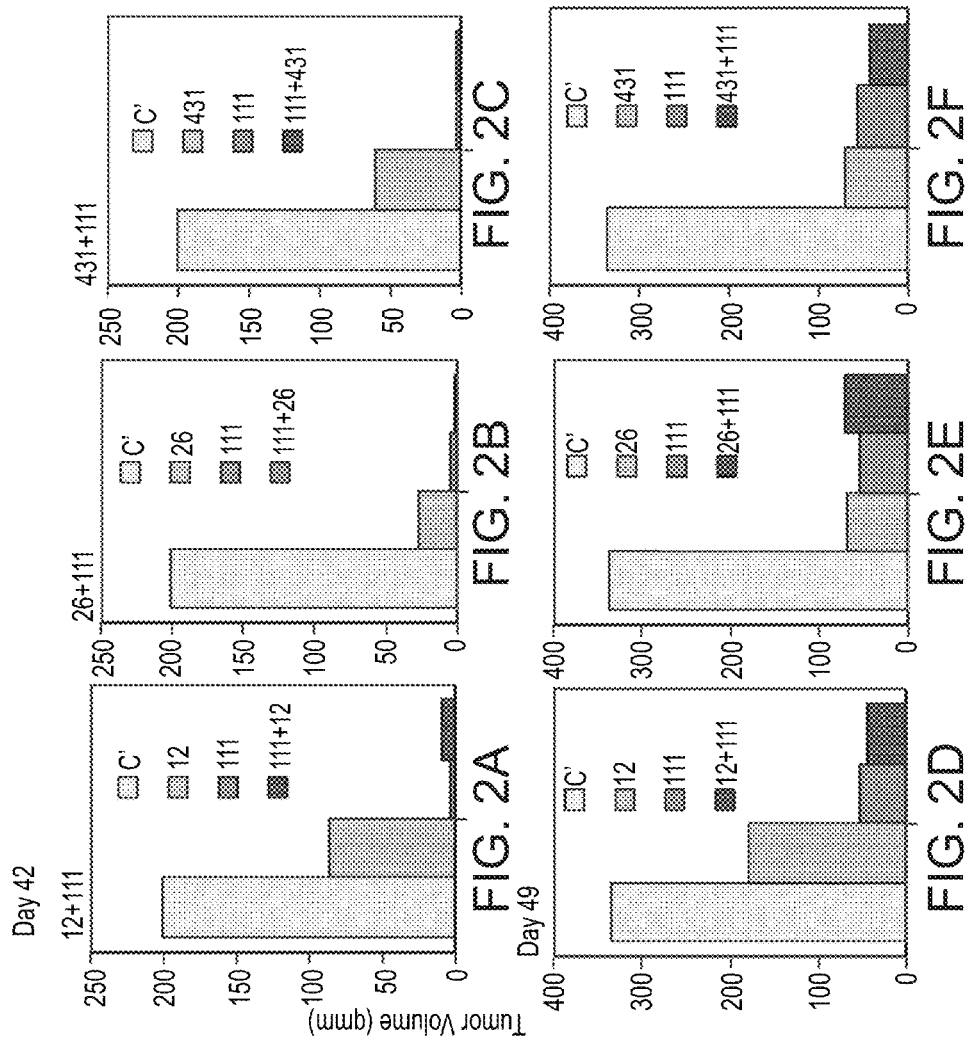

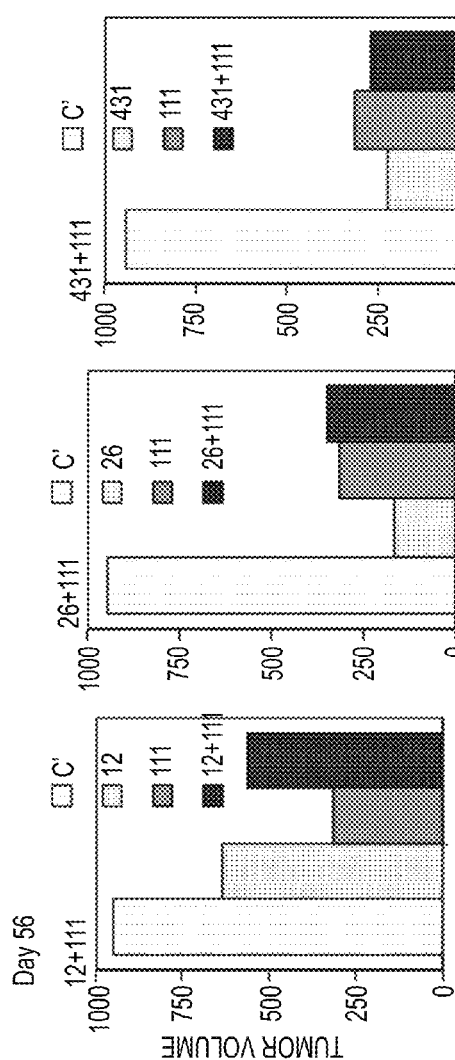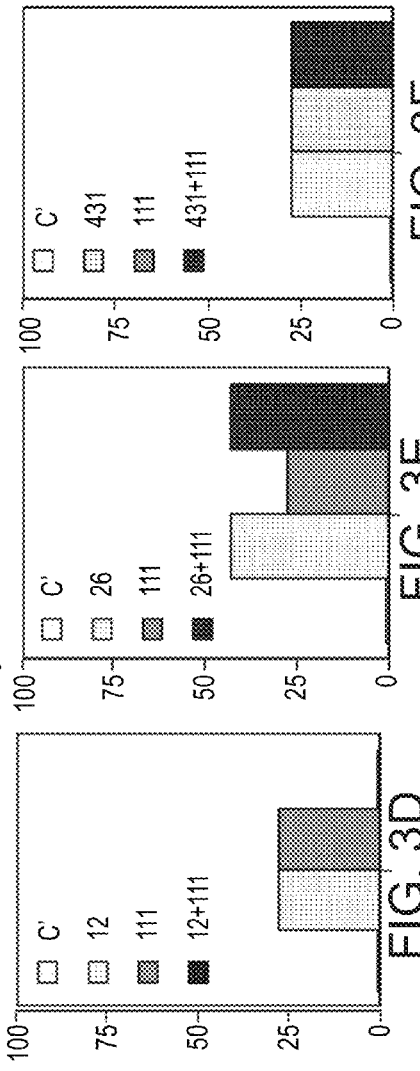

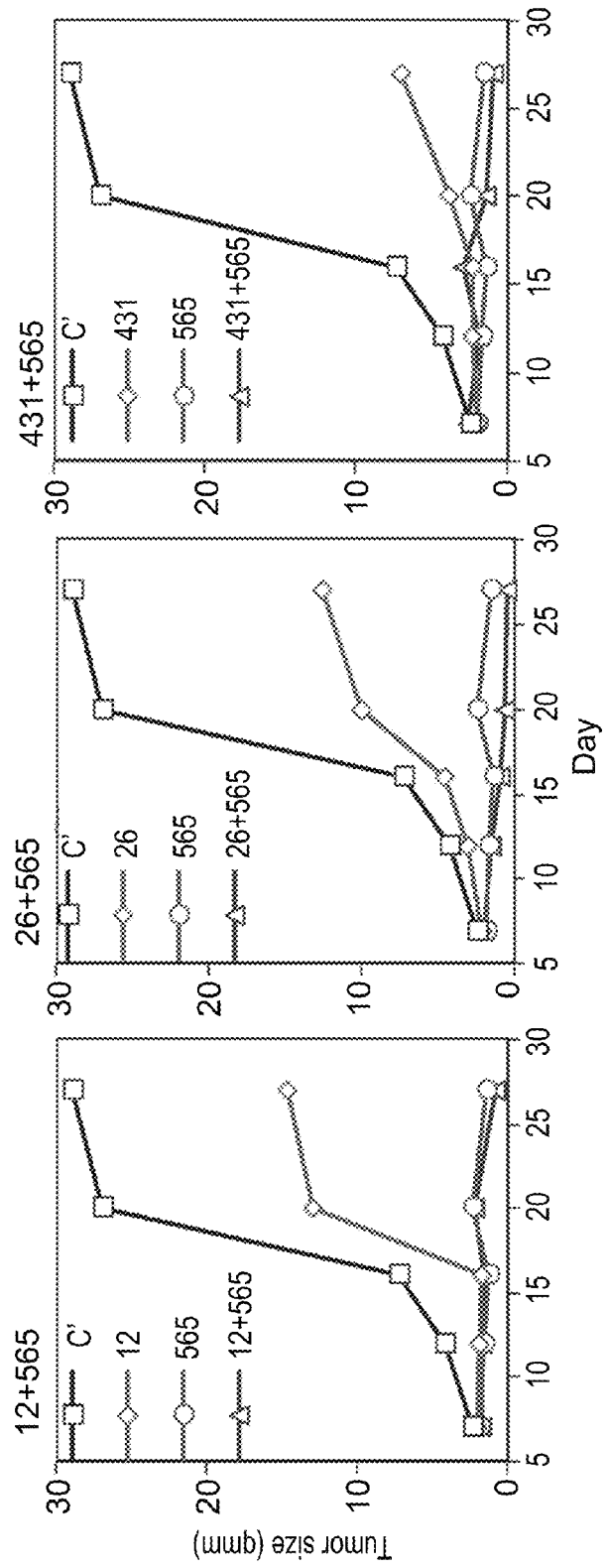

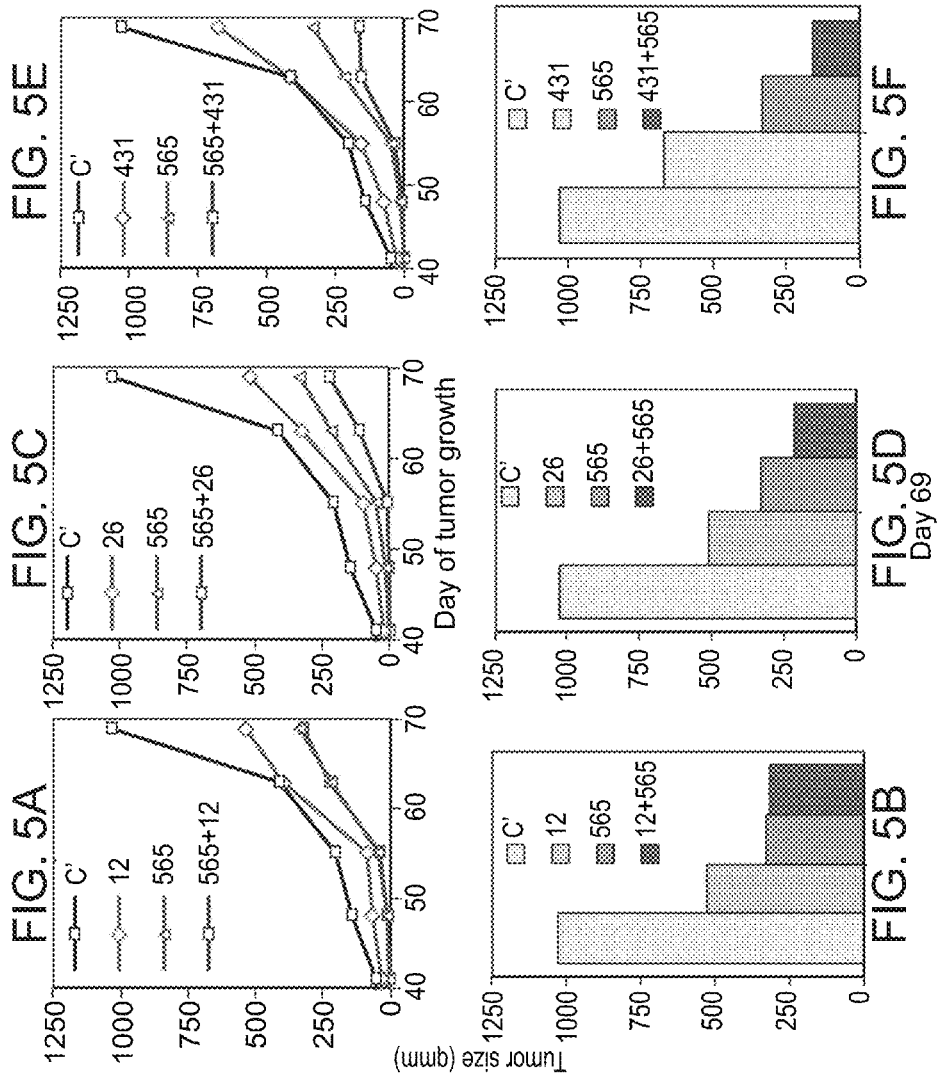

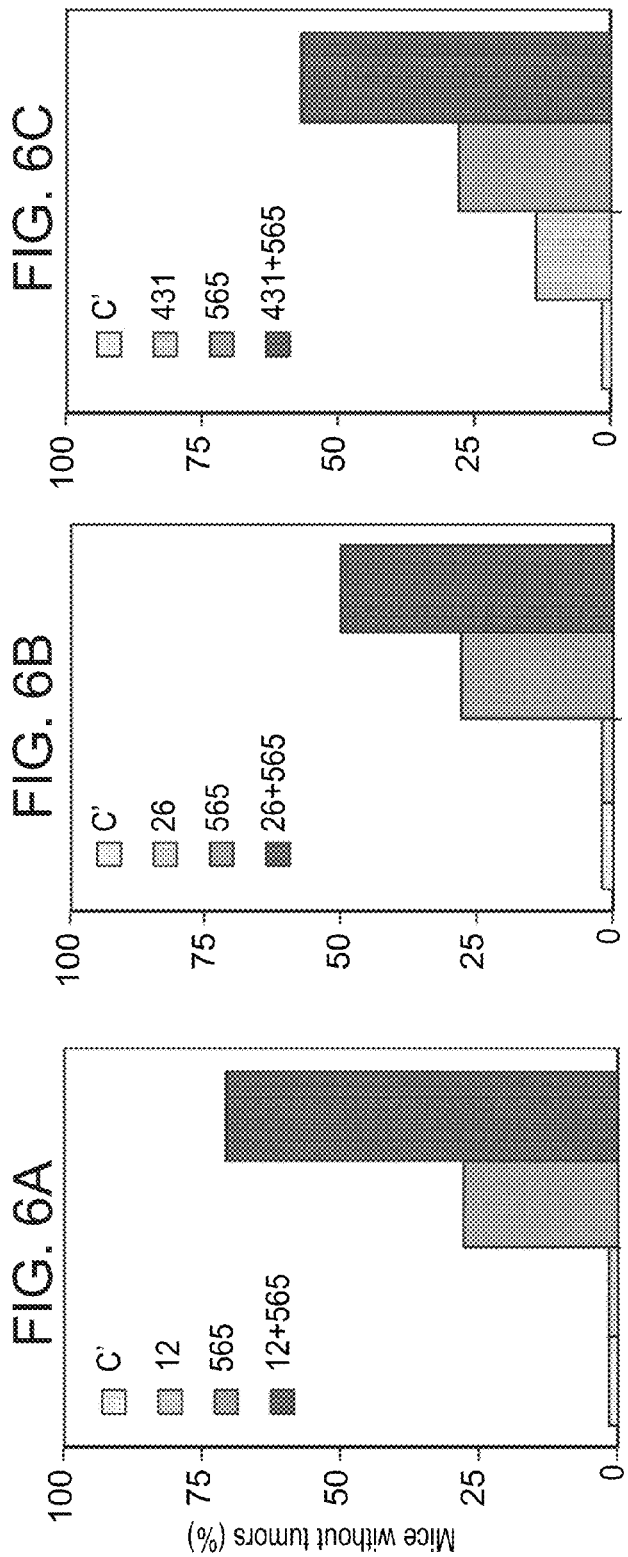

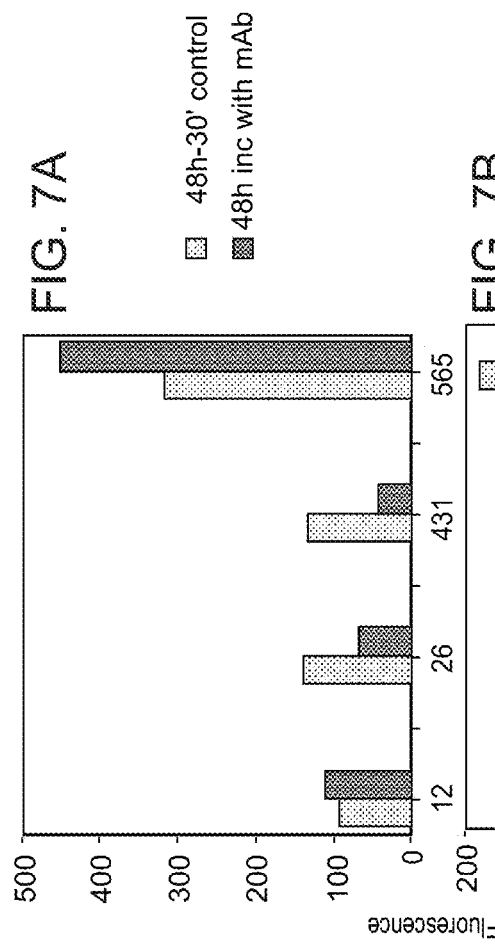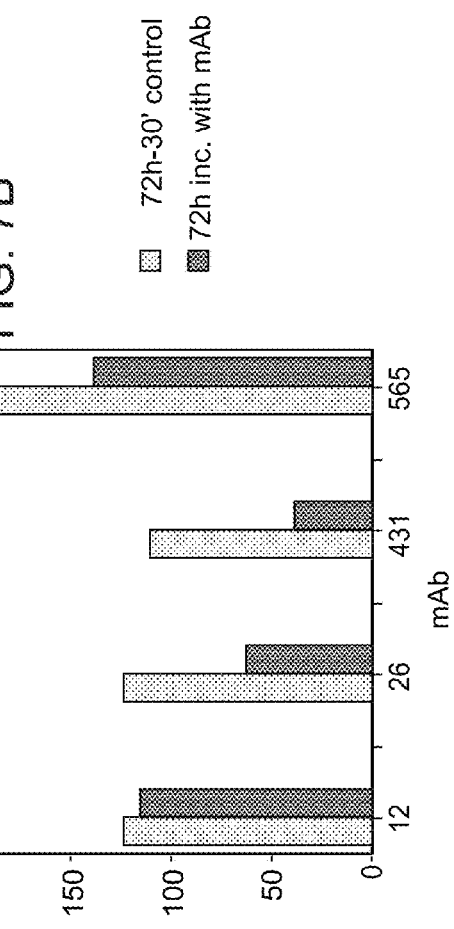

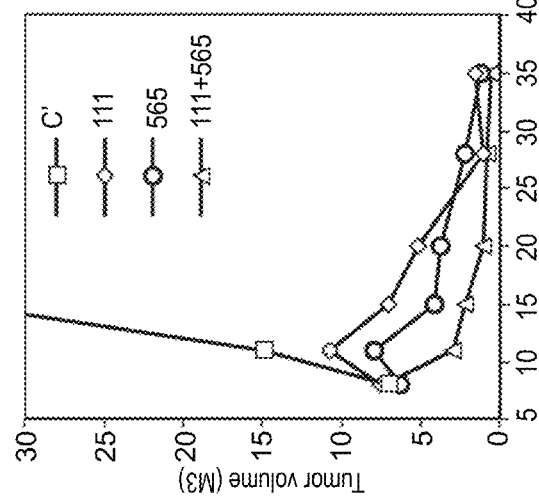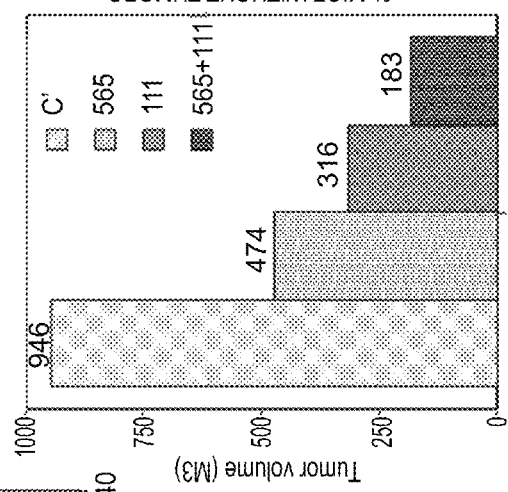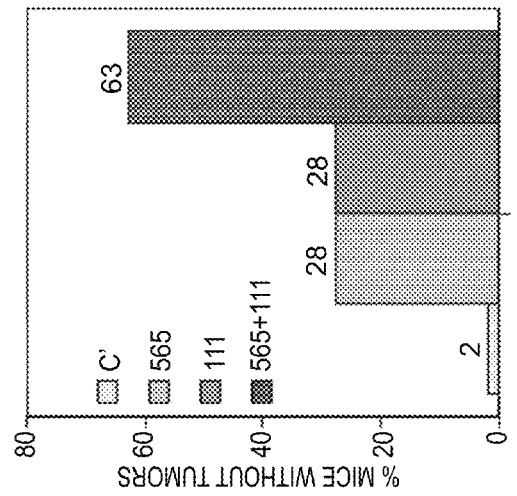

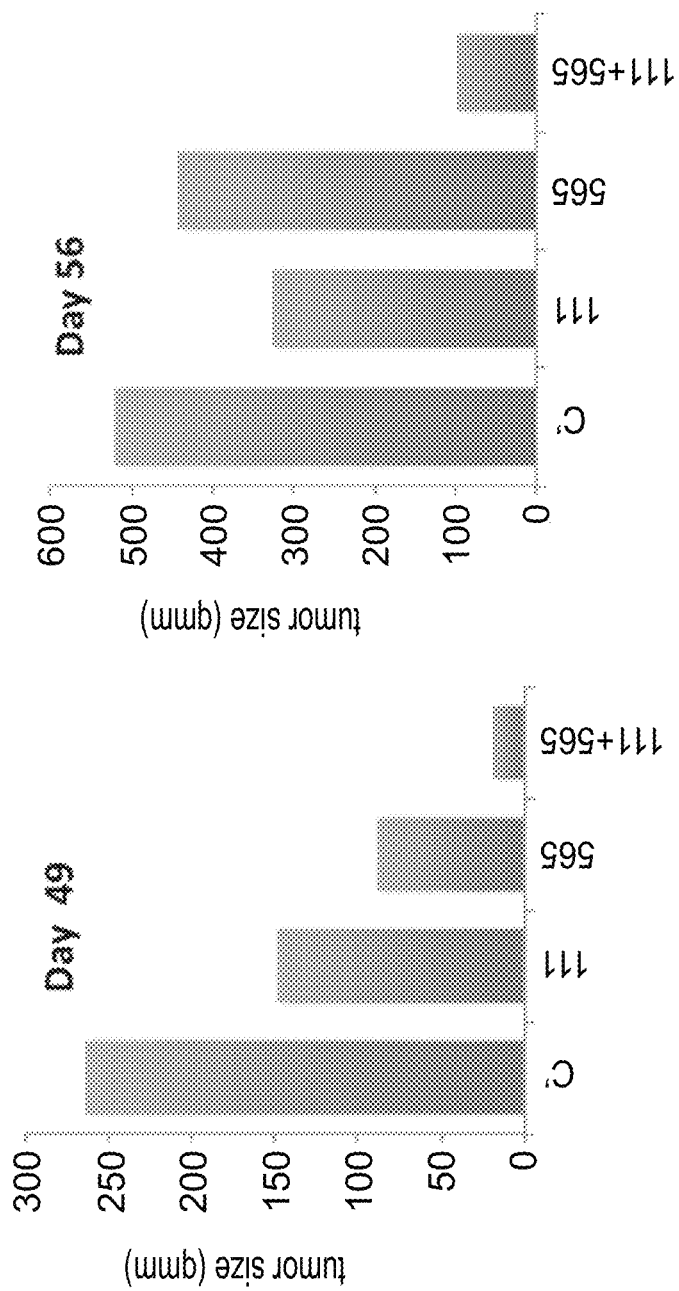

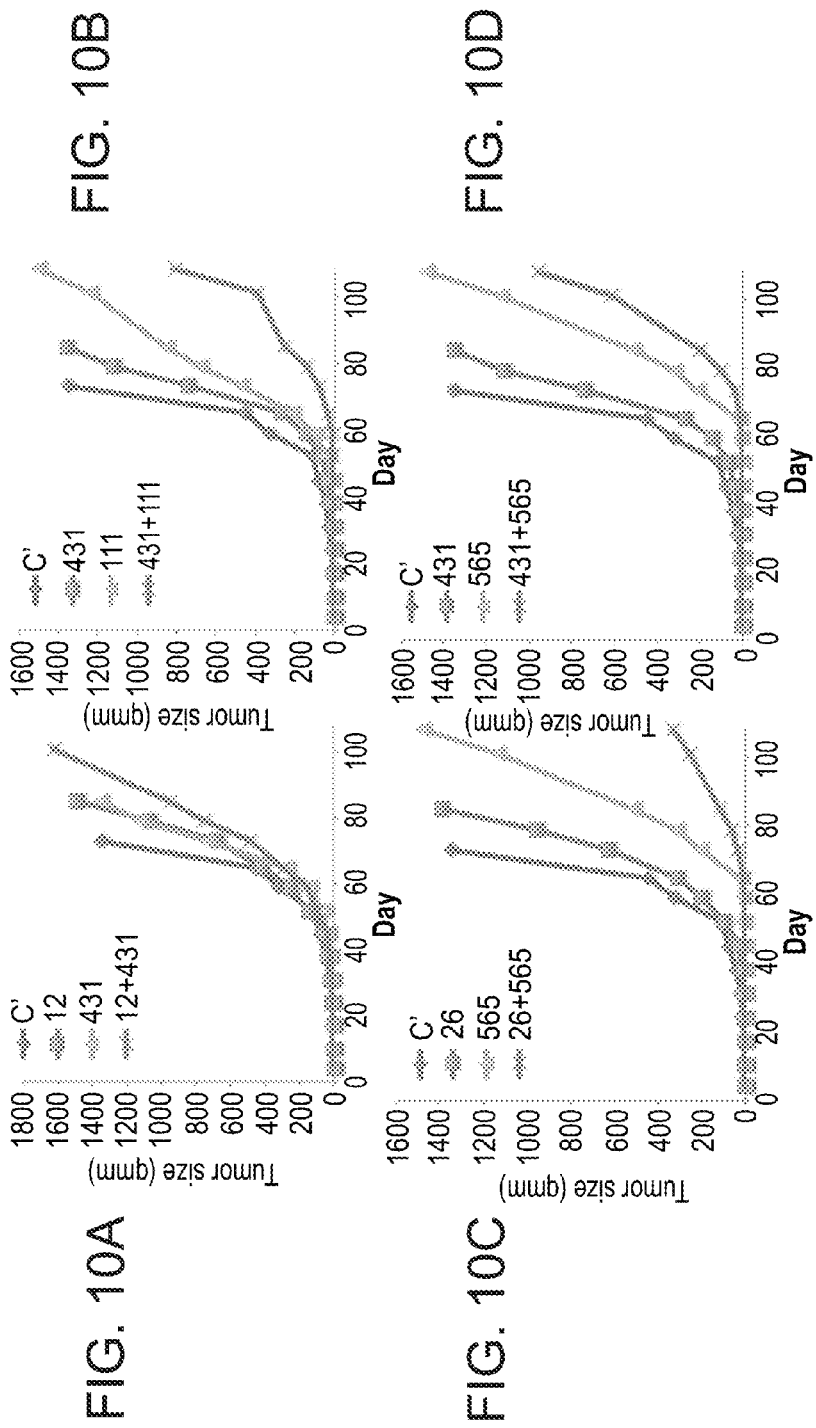

COMBINATIONS OF ANTI ERBB ANTIBODIES FOR THE TREATMENT OF CANCER

RELATED APPLICATIONS

This application is a National Phase of PCT Patent Application No. PCT/IL2012/050176 having International filing date of May 16, 2012, which claims the benefit of priority under 35 USC §119(e) of U.S. Provisional patent application Ser. No. 61/486,362 filed on May 16, 2011. The contents of the above applications are all incorporated by reference as if fully set forth herein in their entirety.

FIELD AND BACKGROUND OF THE INVENTION

The present invention, in some embodiments thereof, relates to combinations of anti ErbB antibodies for the treatment of cancer.

Pancreatic cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%.

Current treatment procedures available for pancreatic cancer have not led to a cure, nor to a substantially improved survival time. Surgical resection has been the only modality that offers a chance at survival. However, due to a large tumor burden, only 10% to 25% of patients are candidates for "curative resection." For those patients undergoing a surgical treatment, the five-year survival rate is still poor, averaging only about 10%.

Antibodies, in particular MAbs and engineered antibodies or antibody fragments, have been tested widely and shown to be of value in detection and treatment of various human disorders, including cancers, autoimmune diseases, infectious diseases, inflammatory diseases, and cardiovascular diseases. The clinical utility of an antibody or an antibody-derived agent is primarily dependent on its ability to bind to a specific targeted antigen associated with a particular disorder.

Tumor inhibition by mAbs is generally attributed to recruitment of effector arms by the antibodies as natural killer cells or by an antibody-dependent cell-mediated cytotoxicity (ADCC). Interaction of receptors with specific mAbs may obstruct cell function in other ways. MAbs can inhibit specific ligand binding, block heterodimerization or induce receptor internalization, thus directly decreasing the mitogenic signal. The evidence of inhibition of receptor phosphorylation or induction of receptor internalization in tumor cells argues in favor of other mechanisms induced directly by the mAb such as apoptotic or cytostatic signal transduced through the receptor. Thus, inhibition of tumor growth by mAbs can be attributed to a number of mechanisms investigated so far and probably to other yet unknown.

Interestingly, mAbs seem to display a synergistic effect when combined with chemotherapy, probably due to interruption of ErbB-2-driven survival pathways [Ben-Kasus T, Schechter B, Sela M, Yarden Y (2007) Cancer therapeutic antibodies come of age: Targeting minimal residual disease. *Mol. Oncology* 1: 42-54.]. Still another strategy, relevant to pancreatic cancer, combines antibodies to EGFR and to ErbB-2 [Larbouret C, Robert B, Navarro-Teulon I, Thezenas S, Ladjemi M Z, Morisseau S, Campigna E, Bibeau F, Mach J P, Pelegrin A, Azria D (2007) In vivo therapeutic synergism of anti-epidermal growth factor receptor and anti-HER2 monoclonal antibodies against pancreatic carcinomas. *Clin Cancer Res* 13: 3356-62; and WO 2007/076923].

Other art documents related to antibody combinations in the treatment of cancer include:
Drebin J. A. et al., Oncogene 2(3):273-277, 1988;
Kasprzyk et al., Cancer Res. 52(10):2771-2776, 1992;
Harwerth et al., Br. J. Cancer 68(6):1140-1145, 1993;
Spiridon et al. Clin. Cancer Res. 8:1720-1730, 2002;
Friedman et al. Proc. Natl. Acad. Sci. (2005) 102:1915-1920;
U.S. Pat. No. 7,498,142; and
WO2010/029534.

SUMMARY OF THE INVENTION

According to an aspect of some embodiments of the present invention there is provided an article-of-manufacture comprising a packaging material identified for treating cancer, packaging:
(i) an anti-EGFR antibody comprising the CDR sequences of anti EGFR 565 (CNCM Deposit Number I-4262); and
(ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112),
or
(iii) an anti-EGFR antibody comprising the CDR sequences of anti EGFR 111 (CNCM Deposit Number I-4261); and
(iv) an anti-ErbB-2 antibody comprising the CDR sequences of anti ErbB-2 L431 (CNCM Deposit Number I-4115).

According to an aspect of some embodiments of the present invention there is provided a pharmaceutical composition comprising as active ingredients:
(i) an anti-EGFR antibody comprising the CDR sequences of anti EGFR 565 (CNCM Deposit Number I-4262); and
(ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112),
or
(iii) an anti-EGFR antibody comprising the CDR sequences of anti EGFR 111 (CNCM Deposit Number I-4261); and
(iv) an anti-ErbB-2 antibody comprising the CDR sequences of anti ErbB-2 L431 (CNCM Deposit Number I-4115)
and a pharmaceutically acceptable carrier or diluent.

According to some embodiments of the invention, the active ingredients are in a co-formulation.

According to some embodiments of the invention, the active ingredients are in separate formulations.

According to an aspect of some embodiments of the present invention there is provided a method of treating cancer in a subject in need thereof, the method comprising administering to the subject a therapeutically effective amount of:
(i) an anti-EGFR antibody comprising the CDR sequences of anti EGFR 565 (CNCM Deposit Number I-4262); and
(ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112), thereby treating cancer in the subject.

According to an aspect of some embodiments of the present invention there is provided:
  (i) An anti-EGFR antibody comprising the CDR sequences of anti EGFR 565 (CNCM Deposit Number I-4262); and
  (ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112) for use in treating cancer.

According to an aspect of some embodiments of the present invention there is provided a method of treating pancreatic cancer in a subject in need thereof, the method comprising administering to the subject a therapeutically effective amount of:
  (i) an anti-EGFR antibody comprising the CDR sequences of anti EGFR 565 (CNCM Deposit Number I-4262); and
  (i) an anti-EGFR antibody comprising the CDR sequences of anti EGFR 111 (CNCM Deposit Number I-4261),
  thereby treating cancer in the subject.

According to an aspect of some embodiments of the present invention there is provided
  (i) an anti-EGFR antibody comprising the CDR sequences of anti EGFR 565 (CNCM Deposit Number I-4262); and
  (i) an anti-EGFR antibody comprising the CDR sequences of anti EGFR 111 (CNCM Deposit Number I-4261) for use in treating pancreatic cancer.

According to an aspect of some embodiments of the present invention there is provided a method of treating pancreatic cancer in a subject in need thereof, the method comprising administering to the subject a therapeutically effective amount of a single anti ErbB-2 antibody comprising the CDR sequences of anti ErbB-2 N12 According to an aspect of some embodiments of the present invention there is provided an anti ErbB-2 antibody comprising the CDR sequences of anti ErbB-2 N12 (CNCM Deposit Number I-4112), when used as a single antibody for treating pancreatic cancer.

According to some embodiments of the invention, at least one of the antibodies is a humanized or partially humanized antibody.

According to some embodiments of the invention, the cancer is pancreatic cancer.

According to some embodiments of the invention, the cancer expresses moderate to high levels of EGFR (above $2 \times 10^5$ molecules/cell) and low levels of ErbB-2 (below $1 \times 10^5$ molecules/cell).

According to some embodiments of the invention, the cancer is selected from the group consisting of breast cancer, ovarian cancer, pancreatic cancer, prostate cancer, lung cancer and head and neck cancer.

According to some embodiments of the invention, the pancreatic cancer comprises a Ras mutation.

According to some embodiments of the invention, the administering comprises multiple administrations.

According to some embodiments of the invention, the multiple administrations comprise weekly administrations.

According to some embodiments of the invention, the method further comprising subjecting the subject to a therapy selected from the group consisting of a radiotherapy and a chemotherapy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-F are bar graphs showing the effect of individual antibodies or antibody combinations including anti EGFR 111 and anti HER2 (12, 26 and 431) in reducing pancreatic tumor growth on days 42 or 49 following pancreatic tumor cells injection.

FIGS. 3A-F are bar graphs showing the effect of individual antibodies or antibody combinations (anti ErbB1-111); and anti ErbB2-12, 26 and 431) in reducing pancreatic tumor growth on day 56 following pancreatic tumor cells injection (tumor volume is shown in the upper panels).

FIGS. 4A-C are graphs showing the effect of individual antibodies or antibody combinations including anti EGFR 565 and anti HER2 (12, 26 and 431) in reducing pancreatic tumor growth at an early stage (till day 27).

FIGS. 5A-F are graphs showing the effect of individual antibodies or antibody combinations including anti EGFR 565 and anti HER2 (12, 26 and 431) in reducing pancreatic tumor growth at later stages (i.e., days 41-69).

FIGS. 6A-C are bar graphs showing the effect of individual antibodies or antibody combinations including anti EGFR 565 and anti HER2 (12, 26 and 431) as presented by percent of absence of tumors on day 69.

FIGS. 7A-B are bar graphs showing surface receptor levels of cells incubated with the indicated antibodies or antibody combination for 48 h or 72 h in comparison to cells incubated with medium alone.

FIGS. 9A-C show the efficacious synergy associated with the treatment using the combination of mAbs 565 and 111 as presented by effect of treatment on days 7, 4, 21 up to 35 (FIG. 9A); average tumor size in FIG. 9B and presence of no tumors or tiny tumors on day 56 (FIG. 9C).

FIGS. 9D-E are histograms showing reduction in pancreatic tumor growth with homo-combination of 111+565 and different treatment schedules. Mice were injected with BXPC3 cells intradermally and then were treated with 4 injections of mAbs or their combinations in days 8, 14, 18 and 22. After a two-week interval the mice were re-administered with the antibodies on days 36 and 41.

FIGS. 10A-D are graphs showing the effect of long term injections of anti ErbB-1 and anti ErbB-2 antibodies or combinations of same of BXPC3 tumor size.

DESCRIPTION OF SPECIFIC EMBODIMENTS OF THE INVENTION

Figures 1A, 1B, 1C:
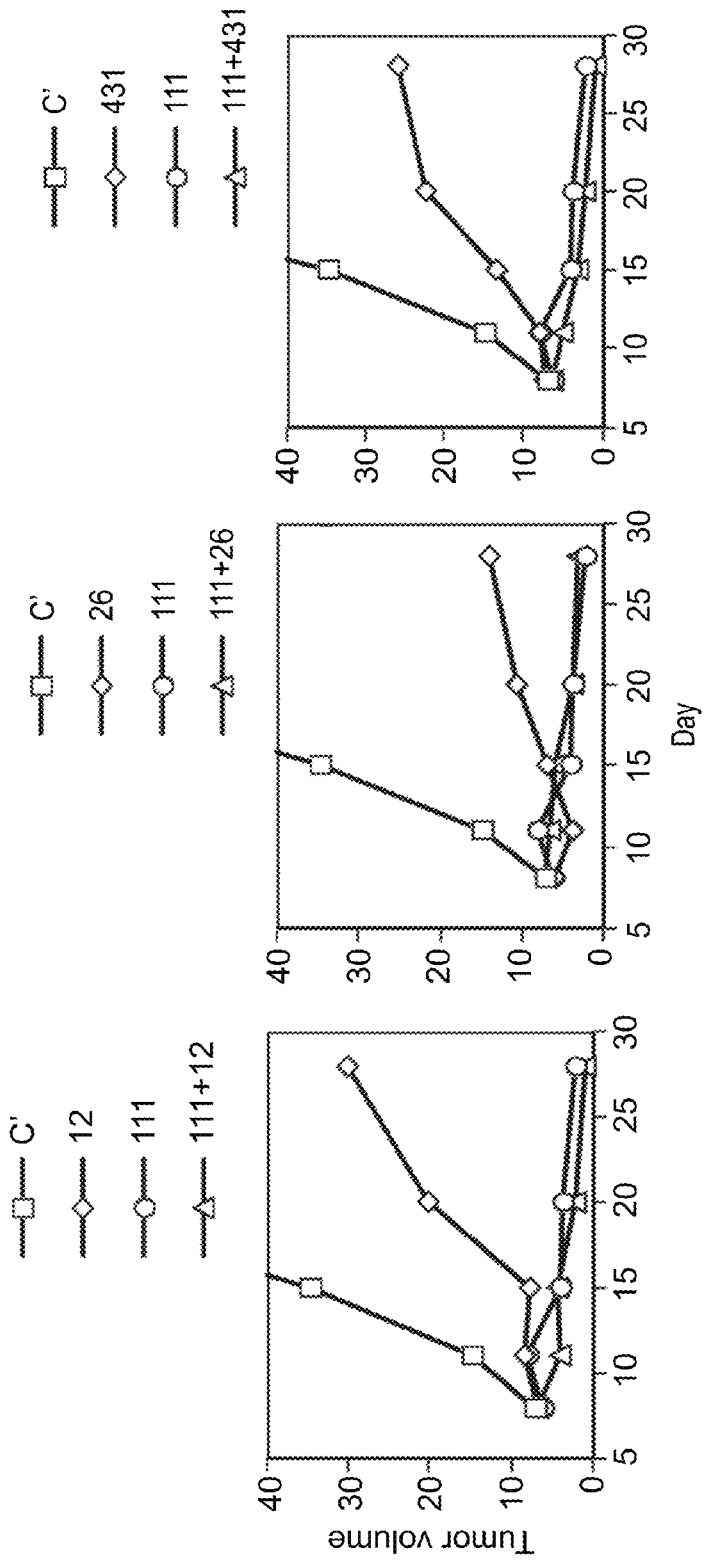
FIGS. 1A-C are graphs showing the effect of individual antibodies or antibody combinations including anti EGFR 111 and anti HER2 (12, 26 and 431) in reducing pancreatic tumor growth at early stage.
Figure 8:
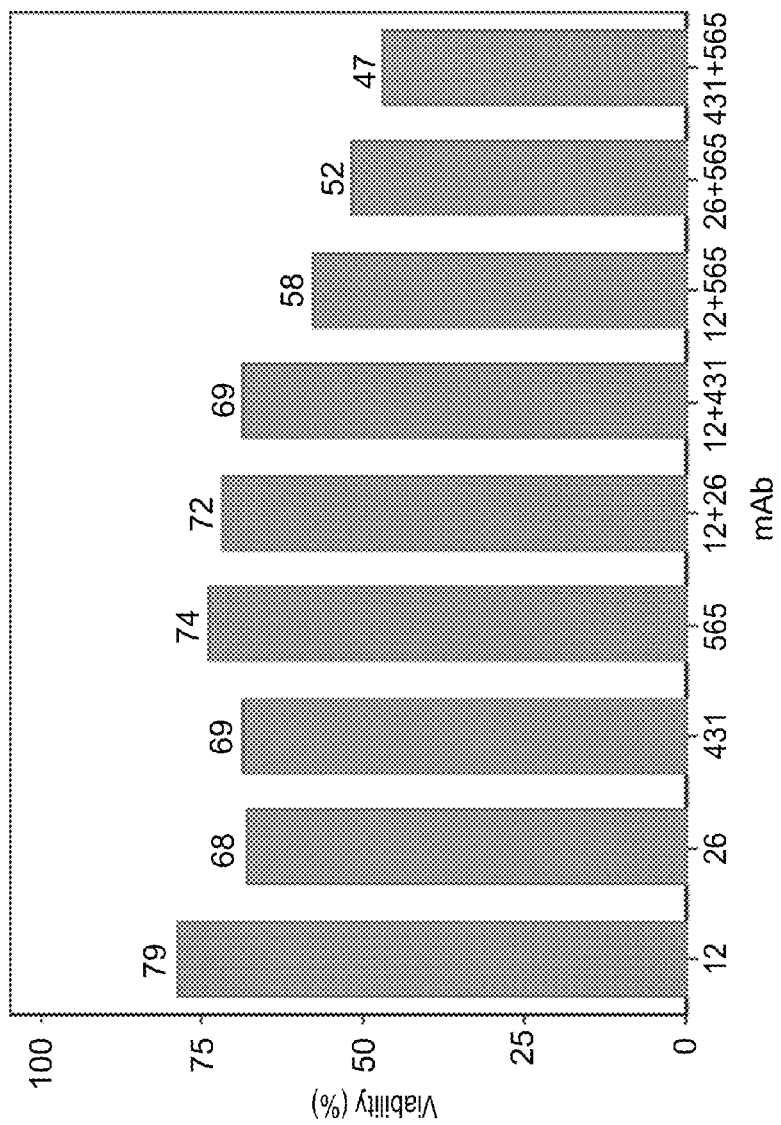
FIG. 8 is a bar graph showing the effect of mAbs, alone or in combination, on viability of BXPC-2 cells in vitro. Cells incubated with mAbs for 72 hr in culture were stained with crystal violet for evaluation of viable cells.
Figure 11A:
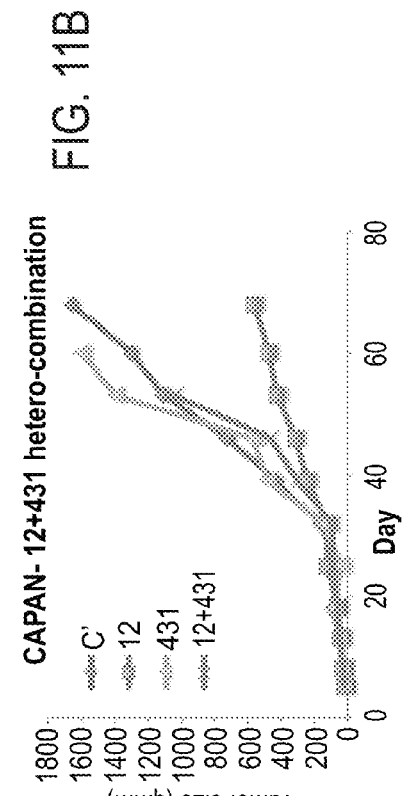
FIGS. 11A-D shows the effect of N12 and L26 in homo or hetero-combinations (i.e., with other anti ErbB-2 antibodies or anti EGFR antibodies, respectively) on CAPAN tumor growth (i.e., Ras mutated pancreatic cancer).
Figure 11B:
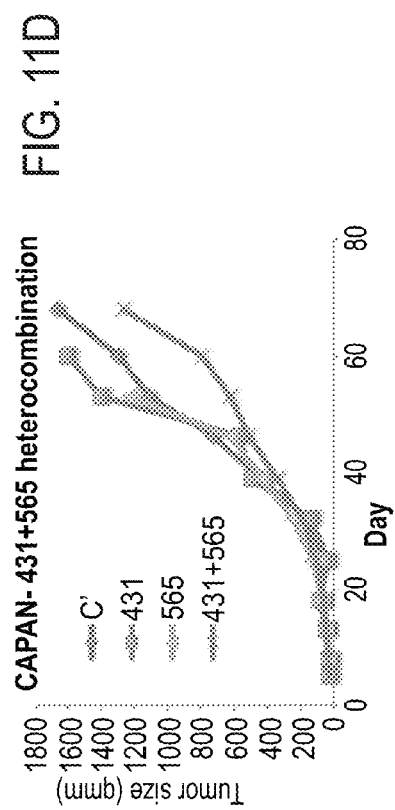
Figure 11C:
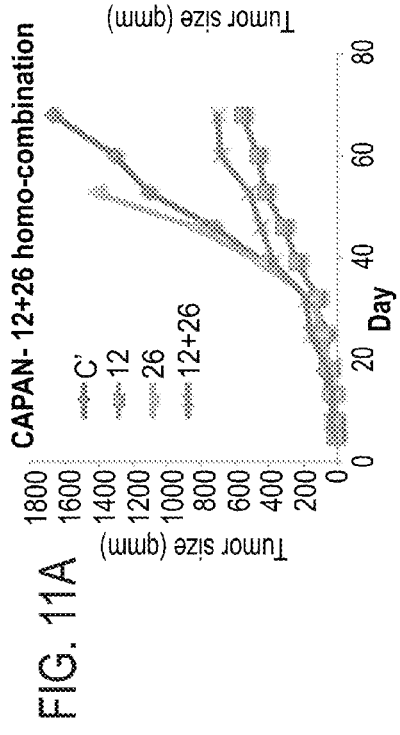
Figure 11D:
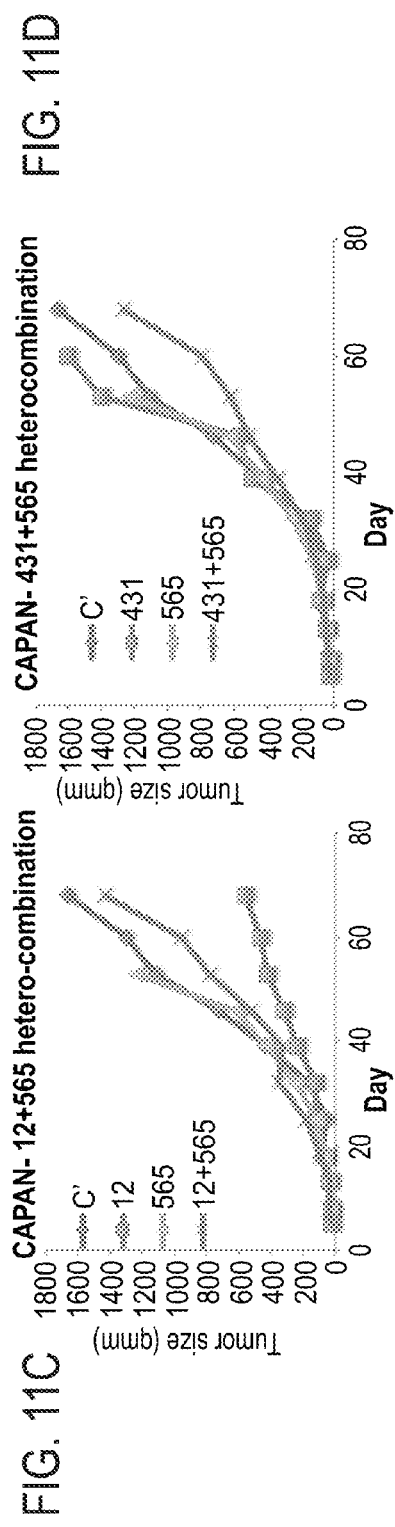

The present invention, in some embodiments thereof, relates to combinations of anti ErbB antibodies for the treatment of cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Pancreatic cancer (PC) carries the highest mortality rate of any cancer type.

Although minor advances in chemotherapy have been made, the mortality rate has remained the same over the last several decades. Clinical trials examining therapies targeting the epidermal growth factor (EGFR), vascular endothelial growth factor (VEGF), specific mutated proteins such as K-ras, immunotherapy employing tumor-associated antigens, and biologic therapy such as TNFerade (GenVec, Inc., Gaithersburg, Md.) have all failed to substantially improve survival.

Pancreatic tumor is characterized by moderate to high overexpression of EGFR and low levels of ErbB-2. The significance of EGFR overexpression in pancreatic cancer is still unclear [Mahipal et al. Med Oncol. 2011 Jan. 25. (Epub ahead of print)].

While reducing the present invention to practice and searching for alternative modalities to the treatment of pancreatic cancer and other tumors exhibiting similar ErbB expression pattern, the present inventors have uncovered through laborious experimentation and screening novel outstanding combinations of anti ErbB receptor antibodies that are capable of inhibiting the growth of pancreatic tumors.

As is illustrated hereinbelow and in the Examples section that follows, the present inventors have shown that a combination of anti EGFR monoclonal antibodies including 565 and 111 is effective in reducing pancreatic tumor volume (i.e., BXpc-3 pancreatic carcinoma) at early stages and late stages of tumor growth (FIGS. 9A-E). It is believed that the combination of two mAbs against distinct sites of the receptor (i.e., 565+111 to EGFR), cross-link multiple receptors and the synergy observed is attributed to the ability of the antibodies to form large antigen-antibody lattices or aggregates at the cell surface since they are directed at distinct epitopes on the receptor. The aggregates collapse into the cytoplasm, undergo intracellular degradation in lysosomes and disappear from the receptor resulting in attenuated ligand-induced signaling.

Additionally, the present inventors have uncovered combinations of antibodies directed at EGFR and ErbB-2 that are surprisingly effective in reducing pancreatic tumor growth even though ErB-2 is expressed only to a low extent on these tumors. As is shown in FIGS. 4-6, 8 and 10, the combination of 565+L431; as well as L26+565 have displayed synergistic activity in inhibiting pancreatic tumor growth. Likewise, co-administration of 111 and L431 synergized in the inhibition of pancreatic cancer (FIG. 10B).

In the case of two mAbs each against a distinct receptor, the effect is expected to emerge from the damaging influence exerted through each receptor, which synergizes or potentiates each other to form a combined loss of function, which is more potent then the damage caused by each mAb alone. Interestingly, both anti ErbB-2 antibodies of the claimed combinations inhibit heterodimerization of ErbB-2.

It is thus expected that the antibody combinations disclosed herein are effective in treating pancreatic cancer and tumors of similar nature in terms of ErbB expression pattern.

Thus according to an aspect of the invention there is provided an article-of-manufacture comprising a packaging material identified for treating cancer, packaging:

(i) an anti-EGFR antibody comprising the CDR sequences of anti EGFR 565 (CNCM Deposit Number I-4262); and (ii) an anti-ErbB-2 antibody comprising the CDR sequences of anti ErbB-2 L431 (CNCM Deposit Number I-4115, also referred to as "431"), anti ErbB-2 L26 (CNCM Deposit Number I-4113, also referred to as "26") or anti ErbB-2 N12 (CNCM Deposit Number I-4112, also referred to as "12");

or (iii) an anti-EGFR antibody comprising the CDR sequences of anti EGFR 111 (CNCM Deposit Number I-4261); and (iv) an anti-ErbB-2 antibody comprising the CDR sequences of anti ErbB-2 L431 (CNCM Deposit Number I-4115).

Accordingly, there is provided a pharmaceutical composition comprising as active ingredients:

(i) an anti-EGFR antibody comprising the CDR sequences of anti EGFR 565 (CNCM Deposit Number I-4262); and (ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112), or (iii) an anti-EGFR antibody comprising the CDR sequences of anti EGFR 111 (CNCM Deposit Number I-4261); and (iv) an anti-ErbB-2 antibody comprising the CDR sequences of anti ErbB-2 L431 (CNCM Deposit Number I-4115).

and a pharmaceutically acceptable carrier or diluent. N12, L26 and L431 have been deposited in the Collection Nationale de Cultures de Microorganismes INSTITUT PASTEUR 25, Rue du Docteur Roux F-75724 Paris CEDEX 15. Antibodies have been deposited under the Budapest Treaty. The materials have been registered on Jan. 13, 2009.

The registration numbers are as follows:

N12 CNCM I-4112;

L26 CNCM I-4113; and

L431 CNCM I-4115.

An anti EGFR antibody combination with a dedicated use in the treatment of pancreatic tumor is also contemplated herein in the following combination (either as an article-of-manufacture or as a pharmaceutical composition):

(i) an anti-EGFR antibody comprising the CDR sequences of anti EGFR 565 (CNCM Deposit Number I-4262); and (i) an anti-EGFR antibody comprising the CDR sequences of anti EGFR 111 (CNCM Deposit Number I-4261), 111.6 (herein referred to as "111") and 565.1 (herein after referred to as "565") have been deposited in the Collection Nationale de Cultures de Microorganismes INSTITUT PASTEUR 25, Rue du Docteur Roux F-75724 Paris CEDEX 15. Antibodies have been deposited under the Budapest Treaty. The materials have been received for deposit on Nov. 26, 2009.

The registration numbers are as follows:

111 CNCM I4261;

565 CNCM I-4262.

A single antibody (i.e., not an antibody combination) treatment of pancreatic cancer (such as that having a Ras mutation) is also contemplated herein.

Thus, there is provided a method of treating pancreatic cancer in a subject in need thereof, the method comprising administering to the subject a therapeutically effective amount of a single anti ErbB-2 antibody comprising the CDR sequences of anti ErbB-2 N12 (CNCM Deposit Number I-4112), thereby treating cancer in the subject.

As used herein "a combination of antibodies" refers to at least two distinct antibodies, having different CDR sequences. According to one embodiment, the combination of antibodies comprises antibodies directed at a single receptor (i.e., EGFR). According to another embodiment, the combination of antibodies comprises antibodies to distinct receptors, essentially one antibody binds specifically to EGFR and the other binds specifically to ErbB-2.

As used herein the phrase "anti tumor activity" refers to prevention of tumor formation and/or reduction of tumor size (e.g., volume) and/or metastasis potential.

The combination of antibodies described herein has combined improved anti tumor activity. As used herein the phrase "combined improved anti tumor activity" refers to at least additive but preferably synergistically improved anti tumor activity as explained hereinabove.

As used herein the term "synergy" refers a total affect that is greater than the sum of the individual contribution of each antibody.

As used herein "ErbB-2" refers to a receptor tyrosine kinase (RTK) of the epidermal growth factor receptor family, ERBB2_HUMAN, P04626, also referred to as HER2, NEU and p185erbB-2.

As used herein "EGFR" refers to a receptor tyrosine kinase (RTK) of the epidermal growth factor receptor family, EGFR_HUMAN, P00533, also referred to as HER1, mENA and ErbB-1.

As mentioned the antibodies contemplated herein comprise the CDR sequences preferably in the same orientation as that of the murine antibodies (i.e., L431, N12, L26, 565 and 111).

Antibodies and forms of humanized (partially or fully) antibodies as well as methods of generating same are described at length in the following sections.

The term "antibody" as used in this invention includes intact molecules as well as functional fragments thereof, such as Fab, F(ab')2, and Fv. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics. The anti ErbB-2 antibodies of the invention bind to an ErbB-2 dimerization site. Conversely, the 565 antibody is directed at the ligand binding site on EGFR.

As mentioned above, the established efficacy of the antibody combinations of the present invention in the elimination, or at least reduction of pancreatic tumors points to their efficacy in the treatment of tumors of similar nature.

Thus, the present invention contemplates the use of the above-mentioned antibody combinations in the treatment of cancer characterized by moderate-to-high expression of EGFR and little or no expression of ErbB-2 in a subject in need thereof.

Specifically, there is provided a method of treating cancer in a subject in need thereof, the method comprising administering to the subject a therapeutically effective amount of:
(i) an anti-EGFR antibody comprising the CDR sequences of anti EGFR 565 (CNCM Deposit Number I-4262); and
(ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112), thereby treating cancer in the subject.

According to another specific embodiment there is provided a method of treating pancreatic cancer in a subject in need thereof, the method comprising administering to the subject a therapeutically effective amount of:
(i) an anti-EGFR antibody comprising the CDR sequences of anti EGFR 565 (CNCM Deposit Number I-4262); and
(i) an anti-EGFR antibody comprising the CDR sequences of anti EGFR 111 (CNCM Deposit Number I-4261),
thereby treating cancer in the subject.

As used herein moderate to high levels of EGFR refers to above about $2\times10^5$ molecules/cell; and low levels of ErbB-2 refers to below about $1\times10^5$ molecules/cell. Methods of assessing surface levels of membrane molecules are well known in the art e.g., FACS (see Example 1 of the Examples section which follows).

Examples of such cancers include, but are not limited to, breast cancer, ovarian cancer, pancreatic cancer, prostate cancer, lung cancer and head and neck cancer.

According to a specific embodiment the cancer is pancreatic cancer.

As used herein "pancreatic cancer" refers to pancreatic adenocarcinomas, adenosquamous carcinomas, signet ring cell carcinomas, hepatoid carcinomas, colloid carcinomas, undifferentiated carcinomas, and undifferentiated carcinomas with osteoclast-like giant cells.

According to a specific embodiment, the pancreatic cancer comprises a mutation in the Ras family, such as mutations that render the Ras protein constitutively active. Examples of oncogenic Ras mutations include but are not limited to $Ras^D$, H-Ras, N-Ras or K-Ras.

Other examples of cancers which can be treated with the antibody combinations described herein include but are not limited to, carcinoma, adenocarcinoma, lung cancer, liver cancer, colorectal cancer, brain, head and neck cancer (e.g., neuro/glioblastoma), breast cancer, ovarian cancer, transitional cell carcinoma of the bladder, prostate cancer, oral squamous cell carcinoma, bone sarcoma, biliary tract cancer such as gallbladder carcinoma (GBC), kidney cancer and pancreatic cancer.

As used herein the term "subject" refers to a mammal, preferably a human subject.

As used herein the term "treating" refers to alleviating or diminishing a symptom associated with a disease (e.g., cancerous disease). Preferably, treating means cures, e.g., substantially eliminates, the symptoms associated with the disease.

Antibodies of the present invention can be administered to an organism per se, or in a pharmaceutical composition where they are mixed with suitable carriers or excipients (either individually or in a co-formulation).

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the antibodies accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations (e.g., weekly or bi-weekly administrations) such as the antibody combination L431+111 see FIG. 10B), with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Typically used models for analyzing the effect of the agents described herein on tumors are provided infra Suitable cells for use in animal models and in vitro analyses include but are not limited to:
Lung cancer:
LKR-13
LKR-10
NSCLC
H1437
H1299
H3255
H1819
H4006
HCC827
HCC2279
Breast
BT-474
Triple negative
MDA 231,
MDA 468
HCC 70,
HCC1187,
HCC1937
Head and Neck cancer:
HN5
PCi 15B
PCI 37A
4PCISSC 103
Ovarian cancer:
OvCar3
SKOV
TOV112

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

It will be appreciated that the antibodies of the present invention can be provided to the individual with additional active agents to achieve an improved therapeutic effect as compared to treatment with the antibodies alone. In such therapy, measures (e.g., dosing and selection of the complementary agent) are taken to adverse side effects which may be associated with combination therapies.

Administration of such combination therapy can be simultaneous, such as in a single capsule having a fixed ration of these active agents, or in multiple capsules for each agent.

Thus, for example, the antibodies of the present invention can be administered along with analgesics, chemotherapeutic agents (e.g., anthracyclins), radiotherapeutic agents, hormonal therapy and other treatment regimens (e.g., surgery) which are well known in the art.

In the treatment of pancreatic cancer standard methods of treatment which can be combined with the antibody treatment of the present invention include, surgery, chemotherapy and radiotherapy.

Generally, treatment of pancreatic cancer depends on the stage of the cancer. The Whipple procedure is the most common surgical treatment for cancers involving the head of the pancreas. This procedure involves removing the pancreatic head and the curve of the duodenum together (pancreato-duodenectomy), making a bypass for food from stomach to jejunum (gastro-jejunostomy) and attaching a loop of jejunum to the cystic duct to drain bile (cholecysto-jejunostomy). It can be performed only if the patient is likely to survive major surgery and if the cancer is localized without invading local structures or metastasizing. It can, therefore, be performed in only the minority of cases.

Cancers of the tail of the pancreas can be resected using a procedure known as a distal pancreatectomy. Recently, localized cancers of the pancreas have been resected using minimally invasive (laparoscopic) approaches.

In patients not suitable for resection with curative intent, palliative chemotherapy may be used to improve quality of life and gain a modest survival benefit. Gemcitabine was approved by the United States Food and Drug Administration in 1998, after a clinical trial reported improvements in quality of life and a 5-week improvement in median survival duration in patients with advanced pancreatic cancer.

On the basis of a Canadian-led Phase III randomised controlled trial involving 569 patients with advanced pancreatic cancer, the US FDA in 2005 licensed the use of erlotinib (Tarceva) in combination with gemcitabine as a palliative regimen for pancreatic cancer. This trial compared the action of gemcitabine/erlotinib to gemcitabine/placebo, and demonstrated improved survival rates, improved tumor response and improved progression-free survival rates (Moore et al. JCO 2005).[49]New trials are now investigating the effect of the above combination in the adjuvant (post surgery) and neoadjuvant (pre-surgery) setting. Addition of oxaliplatin to Gemcitabine (Gem/Ox) was shown to confer benefit in small trials, but is not yet standard therapy.

It is expected that during the life of a patent maturing from this application many relevant therapies will be developed and the scope of the term chemotherapy and radiation therapy is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Specific Combinations of Anti-EGFR and Anti-ErbB-2 are Synergically Effective at Reducing Pancreatic Tumor Size Flow Cytometry.

Cell surface EGFR and ErbB2 expression was analyzed by flow cytometry (fluorescence-activated cell sorting—FACS) using anti-EGFR mAb 565 and anti ErbB2 mAbs 12, 26 and 431. Cells incubated at 4° C. with the mAb for 30 minutes (time 0) or with a mAb for the indicated time period—($0.5\times10^6$, 20 µg/ml) were washed and stained with fluorescent (PE) conjugated anti-mouse Abs (20 µg/ml for 30 min at 4 C in the dark). After washing the cells were subjected to FACS analysis (FACSORT; BD, Franklin Lakes, N.J.). FACS data was analyzed by observing 10,000 events using FlowJo software (Tree Star, Ashland, Oreg.).

Tumor Growth Inhibition In Vivo.

In vivo experiments were done in compliance with standard regulations. Athymic, female nude CD1 mice, 6- to 8-week-old were injected with BxPC-3 ($5\times10^6$) cells s.c. into the right flank. Tumor-bearing mice were randomized in the different treatment groups (7-8 mice/group) when all mice carried palpable tumors. The mice were treated by i.p. injections of mAbs alone or pairs of mAbs at a ratio of 1:1 on days 7, 14 and 21 following tumor injection. Tumor development was followed by weekly measurements with a caliper (D1×D2×D3/2) of tumor volume.

Effect of mAbs on Viability of BXPC3 Cells in Culture.

Antibodies (10 µg/ml) were added to BXPC3 cells ($2\times10^5$/well) grown in 12-well plates at 37° C. for 72 h and cell viability was determined by using the Crystal Violet method. Cell cultures were then washed, fixed for 30 minutes at room temperature (RT) with 12.5% glutaraldehyde in PBS, washed and dried. Crystal violet (0.5 ml of 0.1% solution) was added for 30 minutes at RT while shaking. Cells were washed with water, air-dried and acetic acid (0.5 ml/well of 0.5%) was added for 15 minutes while shaking at RT. Duplicates from each well (100 ul) were transferred to 96 wells Elisa plates and read at 540 nm.

Results

Two mAbs to EGFR (111 and 565) were each tested with each of the three mAbs to Her-2 (12, 26, 431) i.e., 6 combinations, Mice (7-8 mice/group) were treated with a total of 160 µg/injection (80 µg+80 µg in the combination) given to mice carrying palpable tumors, on days 14, 17 and 21 following tumor engraftment.

In Exp. 1 mAb 111 was tested with mAbs 12, 26 and 431. FIGS. 1A-C illustrate the initial stages (days 7-28) of tumor growth after treatment, where mAb 111 was very effective in inhibiting tumor growth (as effective as mAb 565, see FIG. 9A). The three anti Her-2 were partially effective with mAb 26 being better than 12 and 431. Although the tumors were small, it was evident that MAb 111 resulted in decrease in tumor size. The combination-treated tumors also decreased in size even more than tumors treated by mAb 111 alone. It should be noted that mAb 111 in the combination is half the dose as in the single treatment, implying synergy.

Average tumor size increased with time (FIGS. 2A-C) with mAb 111 being the most inhibitory (compared to the control group), but inhibition by mAbs 26 and 431 became more effective (see day 49 FIGS. 2E-F), in fact these two anti Her-2 mAbs were as effective as 111 with 75-80% inhibition at 28 days following last treatment Although the assumption is that the mAbs exert their effect(s) within a few day after inoculation and subsequent growth is a result of decreased tumor cell number by inhibition or eradication of tumor cells at this early stage, some mAbs may have an immediate effect whereas the effect of others may be expressed some time later. The combinations of mAbs 26 and 111 or 431 and 111 were very effective, essentially as effective as the single mAbs with 80% inhibition of the tumor (FIGS. 2A-F, 3A-F). MAb 12 was the least inhibitory but displayed a good synergistic effect with mAb mAb 111. Some of the mice remained tumor free—28% in each group treated with 111, 12, 431 or 111+431 and 43% in groups treated with 26 or 26+111. In summary, no clear synergistic effect was observed between mAb anti EGFR 111 and mAbs anti Her-2-12, 26 and 431 although all these 4 mAbs were markedly inhibitory as single agents.

In Exp. 2 mAb 565 was tested with anti Her2 mAbs 12, 26 and 431. In this experiment tumor growth was slower than in Exp. 1 (tumor inoculums was probably somewhat lower, see FIGS. 9A-B). At the initial stages of tumor growth mAb 565 was as effective as mAb 111 in Exp. 1 and the three anti Her-2 were partially effective with mAb 431 being better than 12 and 26. The tumors were small but it was evident that MAb 565 was very effective and resulted in decrease or shrinkage in tumor size. The combination-treated tumors decreased in size similarly to tumors treated with mAb 565 alone. A synergistic effect was seen later on (FIGS. 5A-F) in combinations of mAbs 565 with 26 and 431: the combination of mAbs 26 and 565 better inhibited tumor growth than each mAb alone and the combination of mAbs 431 and 565 was better than each mAb alone. FIGS. 6A-C show synergy for all combinations when tumor-free mice were analyzed.

FACS analysis of cells incubated for 48 h or 72 h with the mAb 12, did not give any indication of receptor internalization, when compared to cells incubated in medium alone (FIGS. 7A-B). mAbs 26 and 431 caused receptor internalization both in 48 h incubation and 72 h incubation, when compared to medium alone (FIGS. 7A-B). In addition, mAb 565 also showed receptor internalization however only after the longer incubation of 72 h. Viability test indicated that combinations of 565 and 12, 26 or 431 resulted in loss of viability that was greater than the single mAb, mainly 26+565 and 431+565 (FIG. 8), which correlate with the in vivo results. This means that internalization as a result of receptor crosslinking and aggregation does not occur here. Cells are affected in another way which reflects the combined damaging effects of the two mAbs interacting with the two receptors.

Receptor expression (low or high), the specific site to which the mAb binds, interaction (or its inhibition of interaction) between receptors and recruitment of cellular effector arms may all play a role and influence the action of the mAbs. It should be noted that mAbs to a receptor expressed at a very low level on the cell surface can still have a marked inhibitory effect meaning that the extent of receptor expression cannot serve as a guideline for treating cancer by mAbs.

Example 2

Anti EGFR mAbs 111 and 565 Reduce Pancreatic Tumor Size in a Synergic Manner

Results

BXpc-3 pancreatic carcinoma cells that carry EGFR and Her2 receptors on their surface were studied. Measurements of receptor level on the cell surface, using radio-iodine labeled purified mAbs, showed that expression of Her-2 receptors is at a lower level (by 4-7 fold) in comparison to EGFR. Two mAbs to EGFR (111 and 565, one combination) were tested. Mice (7-8 mice/group) were treated with a total of 160n/injection (80 μg+80 μg in the combination) given to mice carrying pulpable tumors, on days 14, 17 and 21 following tumor engraftment.

BXpc3 tumors developed slowly during the first 35 days (shown in FIG. 9A) At this early stage it could be observed that the tumors shrunk in size as a result of treatment by 111, 565 and more so by the combination (FIG. 9A). Growth took off after day 40 where mice treated by 111 and 565 developed tumors more slowly with inhibition of tumor growth of 50 and 70%, respectively (FIG. 9B). The combination between the two mAbs was more effective and reached 80% inhibition of tumor growth. Treatment by mAbs 111 and 565 resulted in cure of tumors in 28% of the mice but with the combination 63% of the mice were without tumors or carried tiny tumors at day 56 where the last treatment was given on day 21 (FIG. 9C). The results were further substantiated in FIGS. 9D-E. Shown is the synergistic activity of 111+565 at days 49 and 56 following administration of each antibody alone or their combinations.

Example 3

Long Term Administrations of Anti ErbB-1 and Anti ErbB-2 and Combinations of Same Anti-EGFR mAbs 111 and 565 or anti ErbB2 mAbs 431 and L26 alone and in combinations 12+431, 111+431, 26+565 and 431+565 were assayed for the effect on the growth on human pancreatic carcinoma BXPC-3 xenografts in nude mice.

BXPC-3 ($5 \times 10^6$) cells were injected into the right flank. Tumor-bearing mice, randomized into groups of 7 mice, were treated by 8 weekly intraperitoneal injections of mAbs (160 μg, starting on day 7) or their combinations (80+80 μg). Tumor development was followed by weekly measurements of tumor volume with a caliper (D1×D2×D3/2).

Results are expressed as increase in tumor size. C', control. All animal studies were performed under protocols approved by the Weizmann Institute of Science Animal Care and Use Committee. FIGS. 10A-D support a synergy between antibodies L26 and 565 as well as 431 and 565.

Example 4

N12 is a Potent Inhibitor of Pancreatic Tumors Carrying a RAS Mutation

CAPAN is a very aggressive tumor carrying a Ras mutation (Capan1 ATCC). Anti ErbB2 mAbs might be involved in the inhibition of ras-mutated pancreatic carcinoma despite the low expression of ErbB2.

Antibodies—Anti-EGFR mAb 565 or anti-ErbB2 mAbs 12, 26 and 431 alone and in combinations 12+26, 12+431, 12+565 and 431+565.

Xenografts of human pancreatic carcinoma ras-mutated in nude mice—cells Capan -1 ($5 \times 10^6$) were injected into the right flank. Tumor-bearing mice, randomized into groups of 6-7 mice, were treated by 8 weekly intraperitoneal injections of mAbs (160 μg, starting on day 7) or their combinations (80 +80 μg). Tumor development was followed by weekly measurements of tumor volume with a caliper (D1×D2×D3/ 2). All animal studies were performed under protocols approved by the Weizmann Institute of Science Animal Care and Use Committee Results are expressed as increase in tumor size. C', control (FIGS. 11A-D).

Results:

mAb L26 (anti-ErbB2) did not inhibit tumor growth (as evidenced by tumor size). Interestingly, the N12 antibody was shown effective in inhibiting tumor growth even when administered as a single antibody and not as a combination with other anti ErbB-2 or EGFR antibodies.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. An article-of-manufacture comprising a packaging material identified for treating cancer expressing EGFR and ErbB-2, packaging:
    (i) an anti-EGFR antibody comprising the CDR sequences of anti EGFR 565 (CNCM Deposit Number I-4262); and
    (ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112);
    or
    (iii) an anti-EGFR antibody comprising the CDR sequences of anti EGFR 111 (CNCM Deposit Number I-4261); and
    (iv) an anti-ErbB-2 antibody comprising the CDR sequences of anti ErbB-2 L431 (CNCM Deposit Number I-4115).

2. A pharmaceutical composition comprising as active ingredients:
    (i) an anti-EGFR antibody comprising the CDR sequences of anti EGFR 565 (CNCM Deposit Number I-4262); and
    (ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112);
    or
    (iii) an anti-EGFR antibody comprising the CDR sequences of anti EGFR 111 (CNCM Deposit Number I-4261); and
    (iv) an anti-ErbB-2 antibody comprising the CDR sequences of anti ErbB-2 L431 (CNCM Deposit Number I-4115)
    and a pharmaceutically acceptable carrier or diluent.

3. The pharmaceutical composition of claim 2, wherein said active ingredients are in a co-formulation.

4. The pharmaceutical composition of claim 2, wherein said active ingredients are in separate formulations.

5. A method of treating cancer expressing EGFR and ErbB-2 in a subject in need thereof, the method comprising administering to the subject a therapeutically effective amount of:

(i) an anti-EGFR antibody comprising the CDR sequences of anti EGFR 565 (CNCM Deposit Number I-4262); and (ii) an anti-ErbB-2 antibody comprising the CDR sequences of anti ErbB-2 L431 (CNCM Deposit Number I-4115), anti ErbB-2 L26 (CNCM Deposit Number I-4113) or anti ErbB-2 N12 (CNCM Deposit Number I-4112), thereby treating cancer expressing EGFR and ErhB-2 in the subject.

6. A method of treating pancreatic cancer in a subject in need thereof, the method comprising administering to the subject a therapeutically effective amount of:

(i) an anti-EGFR antibody comprising the CDR sequences of anti EGFR 565 (CNCM Deposit Number I-4262); and (i) an anti-EGFR antibody comprising the CDR sequences of anti EGFR 111 (CNCM Deposit Number I-4261), thereby treating cancer in the subject.

7. A method of treating pancreatic cancer in a subject in need thereof, the method comprising administering to the subject a therapeutically effective amount of a single anti ErbB-2 antibody comprising the CDR sequences of anti ErbB-2 N12 (CNCM Deposit Number I-4112), thereby treating cancer in the subject.

8. The article-of-manufacture of claim 1, wherein at least one of said antibodies is a humanized or partially humanized antibody.

9. The article-of-manufacture of claim 1, wherein said cancer is pancreatic cancer.

10. The article-of-manufacture of claim 1, wherein said cancer expresses moderate to high levels of EGFR (above $2\times10^5$ molecules/cell) and low levels of ErbB-2 (below $1\times10^5$ molecules/cell).

11. The article-of-manufacture of claim 10, wherein said cancer is selected from the group consisting of pancreatic cancer, prostate cancer, lung cancer and head and neck cancer.

12. The method of claim 5, further comprising subjecting the subject to a therapy selected from the group consisting of a radiotherapy and a chemotherapy.

13. The method of claim 5, wherein said administering comprises multiple administrations.

14. The method of claim 13, wherein said multiple administrations comprise weekly administrations.

15. The method of claim 5, wherein at least one of said antibodies is a humanized or partially humanized antibody.

16. The method of claim 6, wherein at least one of said antibodies is a humanized or partially humanized antibody.

17. The method of claim 5, wherein said cancer is pancreatic cancer.

18. The method of claim 5, wherein said cancer expresses moderate to high levels of EGFR (above $2\times10^5$ molecules/cell) and low levels of ErbB-2 (below $1\times10^5$ molecules/cell).

19. The method of claim 18, wherein said cancer is selected from the group consisting of pancreatic cancer, prostate cancer, lung cancer and head and neck cancer.

* * * * *